United States Patent
Zenker et al.

(10) Patent No.: US 10,369,297 B2
(45) Date of Patent: Aug. 6, 2019

(54) FASTENING ELEMENT AND SYRINGE

(71) Applicant: VETTER PHARMA-FERTIGUNG GMBH & CO. KG, Ravensburg (DE)

(72) Inventors: Jochen Zenker, Ravensburg (DE); Petra Hund, Berg (DE)

(73) Assignee: VETTER PHARMA-FERTIGUNG GMBH & CO. KG (DE)

( * ) Notice: Subject to any disclaimer, the term of this patent is extended or adjusted under 35 U.S.C. 154(b) by 586 days.

(21) Appl. No.: 14/760,241

(22) PCT Filed: Dec. 10, 2013

(86) PCT No.: PCT/EP2013/076017
§ 371 (c)(1),
(2) Date: Jul. 10, 2015

(87) PCT Pub. No.: WO2014/108262
PCT Pub. Date: Jul. 17, 2014

(65) Prior Publication Data
US 2015/0343155 A1 Dec. 3, 2015

(30) Foreign Application Priority Data
Jan. 11, 2013 (DE) .................. 10 2013 200 339

(51) Int. Cl.
*A61M 5/34* (2006.01)
*A61M 39/10* (2006.01)

(52) U.S. Cl.
CPC ............. *A61M 5/347* (2013.01); *A61M 5/34* (2013.01); *A61M 5/344* (2013.01); *A61M 5/345* (2013.01);
(Continued)

(58) Field of Classification Search
CPC ........ A61M 5/3134; A61M 2005/3142; A61M 5/34; A61M 2005/341; A61M 5/344;
(Continued)

(56) References Cited

U.S. PATENT DOCUMENTS 5,702,374 A 12/1997 Johnson
7,559,530 B2 * 7/2009 Korogi ............... A61B 5/15003
251/149.6

FOREIGN PATENT DOCUMENTS

DE 10 2009 007250 A1 7/2010
EP 0 248 979 A1 12/1987
(Continued)

OTHER PUBLICATIONS

International Preliminary Report on Patentability dated Jul. 14, 2015 issued in corresponding International Patent Application No. PCT/EP2013/076017, including English translation of Written Opinion. Total 12 pages.
(Continued)

*Primary Examiner* — Shefali D Patel
(74) *Attorney, Agent, or Firm* — Ostrolenk Faber LLP

(57) ABSTRACT

A fastening element is proposed for fixing an attachment element on an extension piece of a syringe or a carpule, said extension piece having, on an outer face, at least one projection, wherein the fastening element (1) has an annular main body (3) on which a ring element (13) is articulated such that the ring element engages around the extension piece in a mounted state. The ring element has an annular first wall portion (15), which is articulated on the main body (3) via a first bearing area (19), and has an annular second wall portion (17), which is articulated on the first wall portion (15) via a second bearing area (21), wherein the first and second wall portions (15) and (17) are preferably connected to each other resiliently and enclose between
(Continued)

them a free space (23), and wherein the first wall portion (15) is connected resiliently to the main body (3).

11 Claims, 1 Drawing Sheet

(52) U.S. Cl.
CPC . *A61M 39/1011* (2013.01); *A61M 2039/1033* (2013.01); *A61M 2039/1077* (2013.01)

(58) Field of Classification Search
CPC .. A61M 5/345; A61M 5/347; A61M 39/1011; A61M 2039/1033; A61M 2039/1077
See application file for complete search history.

(56) References Cited

FOREIGN PATENT DOCUMENTS

| | | |
|---|---|---|
| WO | WO 2011/064738 A2 | 6/2011 |
| WO | WO 2012/116790 A1 | 9/2012 |

OTHER PUBLICATIONS

International Search Report dated Mar. 4, 2014 issued in corresponding International patent application No. PCT/EP2013/076017.
Written Opinion dated Mar. 4, 2014 issued in corresponding International patent application No. PCT/EP2013/076017.
Notice of Reasons for Rejection dated May 30, 2017 in corresponding Japanese Patent Application No. 2015-552016 (with English language translation)(total 10 pages).

* cited by examiner

US 10,369,297 B2

FASTENING ELEMENT AND SYRINGE

CROSS REFERENCE TO RELATED APPLICATIONS

The present application is a 35 U.S.C. § 371 National Phase conversion of PCT/EP2013/076017, filed Dec. 10, 2013, which claims benefit of German Application No. 10 2013 200 339.0, filed Jan. 11, 2013, the disclosure of which is incorporated herein by reference. The PCT International Application was published in the German language.

TECHNICAL FIELD OF THE INVENTION

The invention relates to a fastening element according to the preamble of claim 1, and to a syringe or carpule according to claim 10.

BACKGROUND OF THE INVENTION

Fastening elements of the type in question here are known. They serve to fix an attachment element on the extension piece of a syringe or carpule or the like, which attachment element can be a needle, a connection element for an injection device or the like. Fastening elements of this type have an annular main body which is provided, for example, with an internal thread into which an external thread of a needle, of a connection element or the like can engage in order to fix an attachment element of this type on a syringe or carpule. The annular main body is provided with a ring element which is mounted pivotably on the main body and which is designed such that it engages around the extension piece of the syringe or carpule in the mounted state of the fastening element and ensures that the fastening element is securely fixed on the extension piece. It has been found that the retaining forces of the fastening element are in some cases inadequate, with the result that the attachment element inadvertently comes loose even during transport of the syringe or carpule, in particular however during the handling of the syringe or carpule, such that the content of the syringe or carpule may be contaminated, which can lead to the loss of very valuable medicaments or may also damage a patient's health.

SUMMARY OF THE INVENTION

The object of the invention is therefore to make available a fastening element that is of the type in question here and that avoids this disadvantage.

To achieve this object, a fastening element of the abovementioned type is made available that has the features referred to in claim 1. It serves to fix an attachment element on the extension piece of a syringe or carpule and has a main body on which a ring element is articulated pivotably. It is characterized in that the ring element has an annular first wall portion, which is articulated on the main body via a first bearing area, and moreover has an annular second wall portion, which is connected to the first wall portion via a bearing area, wherein the two wall portions are preferably connected to each other resiliently and enclose a free space, wherein the first wall area is connected resiliently to the main body. Since the ring element has two wall portions, it is characterized by a high degree of flexibility, which ensures that the ring element is fixed securely on the extension piece of a syringe or carpule, such that the latter can be transported and handled without the danger of the fastening element inadvertently coming loose from the extension piece of the syringe or carpule.

In a preferred illustrative embodiment of the fastening element, provision is made that the ring element has a segmented design, that the first and/or second wall area has a segmented design. It is therefore not necessary that the ring element is designed as a closed ring. It suffices if it has several segments which engage around the extension piece in the mounted state of the fastening element, wherein the first and/or second wall area likewise has a segmented design.

In another preferred illustrative embodiment of the fastening element, provision is made that the first and/or second wall area is held in a spread-open position, by the resilient connection, in the unloaded state. In other words, after the fastening element has been mounted on the extension piece of a syringe or carpule, the resilient connection of the first and/or second wall area to the main body of the fastening element ensures that the ring element bears on the extension piece of the syringe or carpule, so that reliable fixing is ensured by the fact that the annular area is placed on the extension piece in such a way that it finds a secure hold on the at least one projection on the outer face of the extension piece.

A particularly preferred illustrative embodiment of the fastening element is characterized in that at least the second wall area, which bears on the extension piece in the mounted state of the fastening element, can be produced by means of a two-component injection molding technique, wherein components made of harder and softer plastic are used. The components made of harder plastic ensure that the ring element bears on the outer face of the extension piece and finds a secure hold. If forces are applied to the fastening element that could cause the latter to come loose from the extension piece of the syringe or carpule, the ring element catches securely on the at least one projection on the outer face of the extension piece, because the components made of harder plastic provide a high degree of stability of the ring element. The components made of softer plastic ensure high frictional forces on the outer face of the extension piece, such that reliable fixing of the fastening element is obtained.

The object of the invention is also to make available a syringe or carpule by means of which the abovementioned disadvantages can be avoided.

To achieve the stated object, a syringe or carpule is proposed which has an extension piece with at least one projection on the outer face of the extension piece, such that a fastening element can be fixed securely on the extension piece.

BRIEF DESCRIPTION OF THE DRAWINGS

The invention is explained in more detail below with reference to the drawing, in which.

DESCRIPTION OF PREFERRED EMBODIMENTS

Figure 1:
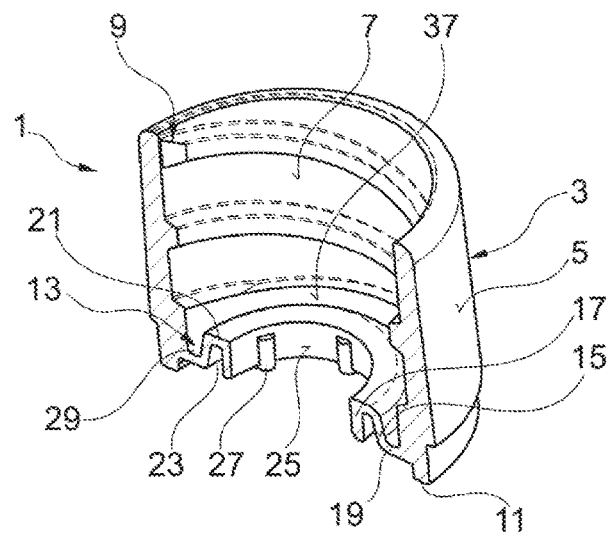
FIG. 1 shows, in a perspective view, a longitudinal section through a first illustrative embodiment of a fastening element

A first illustrative embodiment of a fastening element 1, which can be seen in FIG. 1, has an annular main body 3 shown here in longitudinal section. The main body 3 has an outer face 5 and an inner face 7, and, in the illustrative embodiment shown here, a fastening device can be provided on the inner face 7, which fastening device serves to securely receive an attachment element, preferably a needle, or else a connection element for an injunction device or the like. A fastening element 1 of the type in question here usually has, on its inner face 7, an internal thread 9 which cooperates with an external thread of an attachment element of a needle in order, on the one hand, to fix the needle securely in the fastening element while, on the other hand, the fastening element itself is mounted on an extension piece (not shown here) of a syringe or a carpule. The fixing of an attachment element in the fastening element can also be effected by means of a bayonet catch.

To fix the fastening element 1 on the extension piece of a syringe or carpule, a ring element 13 is provided in the area of the lower free end 11 of the main body 3, which ring element 13 comprises a first wall portion 15 and a second wall portion 17. The ring element is articulated with its first wall portion 15 on the main body 3, specifically via a first bearing area 19. The two wall portions 15 and 17 are connected to each other, specifically via a second bearing area 21.

The two wall areas 15 and 17 are connected to each other via the second bearing area 21 such that a free space 23 remains between the wall areas, and the ring element 13, seen in cross section, is V-shaped or U-shaped. The free space 23 opens out downward in the direction of the lower end 11 of the main body 3.

The first bearing area 19 between the first wall portion 15 and the main body 3 of the fastening element 1 is resilient, such that the first wall area 15 is held in a spread-open position in relation to the inner face 7 of the main body 3 and extends obliquely inward starting from the inner face 7.

The second bearing area 21 between the first wall 15 and the second wall portion 17 can be rigid, such that the two wall portions 15 and 17 remain in a U-shaped or V-shaped arrangement with respect to each other even when the fastening element 1 is mounted on an extension piece of a syringe or carpule (not shown).

Preferably, however, the second bearing area 21 is also resilient, wherein the two wall portions 15 and 17 are held spread apart from each other in the unloaded state, i.e., while the fastening element 1 is not mounted on an extension piece of a syringe or carpule, such that the free space 23 shown in FIG. 1 is obtained between the wall portions 15 and 17. However, the elasticity in the second bearing area 21 is preferably chosen such that, when the fastening element 1 is mounted on an extension piece of a syringe or carpule, the wall portions 15 and 17 are pressed against each other, counter to the spring elasticity in the second bearing area 21, and, in this way, the free space 23 is as it were closed.

When the fastening element 1 is mounted on an extension piece, the elasticity in the first bearing area 19 also means that the first wall portion 15 is placed against the inner face 7 of the main body 3, such that the ring element 13 pushes together as an accordion as it were while the fastening element 1 is mounted on an extension piece of a syringe or a carpule.

At least one projection 27 is preferably provided on the inner face 25 of the second wall portion 17. Projections 27 are preferably distributed at uniform intervals from one another across the inner face 25. In the illustrative embodiment shown here, the projections 27 are strip-shaped and extend over most of the height of the second wall portion 17. Provision is preferably made here that the projections 27 are curved, in particular curved in the shape of an arc of a circle, i.e. they have a partial cylindrical surface rising above the inner face 25 of the second wall portion 17.

The projections 27 can be formed by a technique in which depressions are introduced into the second wall portion 17, and elements that form the projections 27 are fitted into the depressions. It is also conceivable for elements to be glued onto the inner face 25 of the second wall portion 17, which elements then form the projections 27.

FIG. 1 shows that a substantially V-shaped gap 29 is present between the inner face 7 of the main body 3 and the first wall portion 15 issuing from the first bearing area 19, said gap 29 opening upward, i.e. in a direction away from the lower end 11.

It is possible to provide apertures 113 (see FIG. 3) in the first bearing area 19, which forms the bottom of the V-shaped gap 29. These apertures 113 serve to ensure drainage of liquids such that, when using a syringe or carpule provided with the fastening element 1, liquids reaching the gap 29 are able to drain off. The apertures 113 can be varied in terms of their shape, in particular in terms of their extent as seen in the circumferential direction, so as to influence the spring characteristics of the first bearing area 19, i.e. so as to vary the forces with which the first wall area 15 is spread open from inner face 7.

Figure 2:
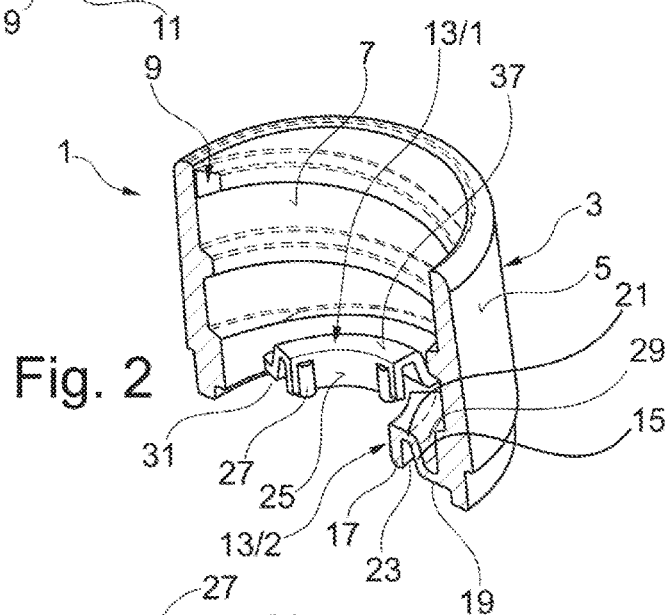
FIG. 2 shows, in a perspective view, a longitudinal section through a second illustrative embodiment of a fastening element.

FIG. 2 shows a modified illustrative embodiment of the fastening element 1. Identical parts are provided with identical reference numbers, and reference may therefore be made in this connection to the description of FIG. 1.

The only difference between the two illustrative embodiments of the fastening element shown in FIGS. 1 and 2 is that the ring element 13 is not designed as a continuous ring in the manner explained with reference to FIG. 1. Instead, the ring element 13 is divided into individual segments, in this case into three segments, of which segments 13/1 and 13/2 can be seen in FIG. 2. Between two adjacent elements there is in each case a space 31, of which the width can likewise be chosen like the number of segments of the ring element. It is therefore entirely possible to provide ring elements that have more than three segments arranged at uniform circumferential intervals, or alternatively just two segments, which are preferably arranged lying opposite each other in the area of the inner face 7 of the main body 3.

Figure 3:
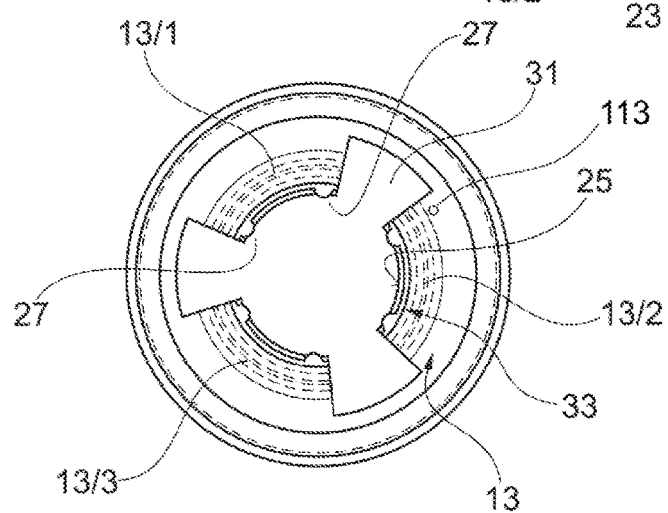
FIG. 3 shows a bottom view of the second illustrative embodiment of the fastening element according to FIG. 2.

FIG. 3 shows the second illustrative embodiment of the fastening element 1 in a bottom view. It thus has a ring element 13 with three segments 13/1, 13/2 and 13/3 arranged at uniform circumferential intervals from each other, with a space 31 provided in each case between two adjacent segments.

It will be seen from FIGS. 2 and 3 that each of the ring segments 13/1, 13/2 and 13/3 has two projections 27, which protrude into the free space in the fastening element 1 enclosed by the ring segments, i.e. protrude into the interior 32 of the fastening element 1.

It was mentioned above that the projections 27 can be elements that are inserted into recesses in the second wall portion 17, but that it is also possible to glue projections 27 onto the inner face 25 of the ring segments of the ring element 13.

It is also possible to insert ring-segment-shaped projection elements 33 with projections 27 into the second wall portion 17 of a ring segment, such that the projections 27 protrude radially as it were into the interior 32 enclosed by the ring element 13 or by the ring segments 13/1 and 13/2 and 13/3.

It is thus possible to insert projection elements 33 with projections 27 into the individual ring segments 13/1 to 13/3. This is also possible by the way in the illustrative embodiment according to FIG. 1: An annular projection element can be inserted into the second wall portion 17 via the free space 23, such that the projections 27 protrude inward.

Particularly preferably, however, provision is made that at least the second wall portion 17 comprises plastic, preferably consists thereof, and that the projections 27, if appropriate also the projection element 33, likewise comprise plastic, in particular consist thereof.

Very particularly preferably, provision is made that the second wall portion 17 and the projections 27, if appropriate also projection elements 33, are produced in a two-component injection molding technique.

It is particularly cost-effective for the entire fastening element 1 with the ring element 13, if appropriate the ring segments 13/1 to 13/3 with the projections 27, which can be made as individual elements or issue from projection elements 33, to be produced in a two-component injection molding technique.

It will be clear from the explanations that the entire second wall portion 17 can also be produced from a softer material, particularly if the first wall portion 15, preferably also the second bearing area 21, is produced from a harder material, such that the ring element 13 or the ring segments 13/1 to 13/3 is/are supported on a projection when the fastening element 1 is fixed on an extension piece of a syringe or a carpule and is subjected to tensile forces which seek to remove the fastening element 1 from the extension piece.

Regarding the function of the fastening element 1 as explained with reference to FIGS. 1 to 3, the following is noted:

The figures show the fastening element 1 in an unloaded state, i.e. separate from an extension piece of a syringe or a carpule. These generally have an extension piece which has a cylindrical shape, but which is in particular slightly conical, wherein the thicker area of the extension piece transitions into the main body of the syringe or carpule.

In the vicinity of this transition, at least one projection is preferably provided which has a shoulder directed away from the free end of the extension piece. After it has been fixed on the extension piece of the syringe or carpule, the fastening element 1 locks behind this extension piece.

In the vicinity of the transition to the main body of the syringe or carpule, a peripheral groove is preferably introduced into the outer face of the extension piece, which groove has a bottom surface whose external diameter is smaller than the external diameter of the outer face of the extension piece in the adjoining area. The groove is thus substantially U-shaped. It suffices if the groove has only one lateral boundary wall, which is arranged on the side of the groove directed toward the free end of the extension piece. The groove thus has a peripheral shoulder which serves as a projection on which the fastening element 1 engages with locking action when it is pushed onto the extension piece of a syringe or a carpule.

The following is noted in particular:

It is assumed below that the extension piece of a syringe or a carpule has a peripheral groove whose boundary shoulder facing in the direction of the free end of the extension piece forms a projection.

The internal diameter of the fastening element 1 is chosen such that the main body 3 can be pushed onto the extension piece. Provision is made that, in the unloaded state of the fastening element 1 as shown in FIGS. 1 to 3, the inner face 25 of the second wall portion 17 has an internal diameter than is smaller than the external diameter in the area of the groove, which is provided on the extension piece.

Thus, when the fastening element 1 is pushed, with its free end 11 to the front, onto an extension piece, the outer face of the extension piece forces the second wall portion 17 radially outward, such that the ring element 13 or the segments 13/1 to 13/3 thereof are moved against the inner face 7 of the main body 3. The second wall portion 17 is forced against the first wall portion 15, such that the width of the free space 23 reduces if the second bearing area 21 is elastic. The two wall portions 17 and 15 can bear on each other. The first wall portion 15 is also widened, such that the width of the gap 29 is reduced until optionally the first wall portion 15 bears on the inner face 7 of the main body 3 of the fastening element 1. The ring element 13 or the segments 13/1, 13/2 and 13/3 thereof are thus pushed together as it were in the manner of an accordion while the fastening element 1 is being mounted onto the extension piece of a syringe or a carpule.

If the fastening element 1 is moved in the axial direction on the extension piece of the syringe or carpule, in the direction of the main body of the syringe or carpule, the ring area 13 finally reaches the area of the at least one projection or the groove which is provided on the outer face of the extension piece. If the ring element, or the segments thereof, is pushed over the at least one projection or the upper lateral boundary face of the groove, the ring element 13 or the segments thereof can project in the direction of the bottom surface of the groove. In other words, the second wall portion 17 can contract again, and, as viewed from the free end of the extension piece, can spring back on the other side of the at least one projection or on the other side of the lateral boundary edge of the groove. The inner face 25 preferably bears on the outer face of the extension piece on the other side of the projection or on the other side of the lateral boundary edge of the groove, such that the fastening element 1 is fixed securely on the extension piece of the syringe or carpule.

In the mounted state of the fastening element 1, the top 37 of the ring element 13, or of the ring segments 13/1 to 13/3, facing away from the lower end 11 of the main body 3 of the fastening element 1 bears on the at least one corresponding projection from the outer face of the extension piece or on the upper lateral boundary face of the groove introduced into the outer face of the extension piece, such that an axial removal of the fastening element 1 from the extension piece is practically excluded. If axial tensile forces act on the fastening element 1, the ring element 13, or the segments 13/1 to 13/3 thereof, is securely held by the at least one projection or the lateral boundary edge of the groove, such that the ring element 13, or the segments 13/1 to 13/3 thereof, under the effect of the axial forces, tilts inwardly in the direction of the outer face of the extension piece about the first bearing area 19, such that the retaining forces with which the fastening element 1 is fixed on the extension piece increase.

The fastening element 1 is preferably also secured against inadvertent rotation on the extension piece of a syringe or a carpule. This is already achieved by the fact that the elastic ring element 13 or the segments thereof are expanded when mounted on the extension piece and, on account of their elastic restoring forces, bear on the outer face of the extension piece with high force. In particular, of course, the second wall portion 17 bears with its inner face 25 on the outer face 107 of the extension piece .

In order to increase the frictional forces, the second wall portion 17 can consist, at least on its inner face 25 or also along its entirety, of a softer material than is chosen for the first wall portion 15. The softer material bears better on the outer face of the extension piece and thus builds up high frictional forces. The harder material of the first wall portion 15 ensures that, viewed in the axial direction, the latter is stable enough to take up axial tensile forces and to ensure a tilting movement of the ring element 13, or of the ring segments 13/1 to 13/3, so that the fastening element 1 is held under the at least one projection or on the upper lateral boundary face of a groove in the outer face of the extension piece.

In order to increase the frictional forces between the second wall portion 17 and the outer face of the extension piece, individual projections 27 on the inner face 25 of the second wall portion 17 can be provided which particularly preferably consist of a softer material and thus bear very well on the outer face of the extension piece 105 and build up frictional forces that prevent inadvertent rotation of the fastening element 1 in relation to the extension piece of the syringe or carpule but that also prevent removal in the axial direction.

Particularly high resistance forces are built up if the second bearing area 21 between the first wall portion 15 and the second wall portion 17 is made relatively rigid. However, in order to reduce the forces that are required when fitting the fastening element 1, this second bearing area 21 is preferably made elastic such that, in an unloaded state, the two wall areas 15 and 17 are held spread apart from each other, thus giving the free space 23.

In order to vary the retaining forces, the elasticity of the second bearing area 21, but also of the first bearing area 19, can be changed. If appropriate, the apertures 113 mentioned above can also be provided in the first bearing area 19. It is thus possible to set the spreading forces that seek to keep the first wall portion 15 away from the inner face 7 of the main body 3 in the spread-open state or to force it against the outer face of an extension piece.

It is clear from FIGS. 1 and 2 that the main body 3 can be made stronger in the area of the free end 11. Here, the wall of the main body 3 is slightly thicker than is the case above the ring element 13 or the ring segments 13/1 to 13/3.

What is claimed is:

1. A fastening element for fixing an attachment element on an extension piece of a syringe or a carpule, said extension piece having, on an outer face thereof, at least one projection, wherein the fastening element comprises a one-piece structure having an annular main body provided with an internal thread into which an external thread of the attachment element of a needle can engage, and wherein said annular main body further comprises a ring element articulated on an inner face thereof such that the ring element engages around the extension piece in a mounted state,
   wherein the ring element
      has an annular first wall portion, which is articulated on the main body via a first bearing area, and
      has an annular second wall portion, which is articulated on the first wall portion via a second bearing area, wherein
      the first and second wall portions enclose between them a free space, wherein
      the first wall portion is connected resiliently to the main body, wherein
      when the fastening element is mounted on the extension piece of the syringe or the carpule, the first wall portion is widened and a gap between the inner face and the first wall portion is reduced, such that the ring element is pushed together in a manner of an accordion, while the fastening element is mounted on the extension piece.

2. The fastening element according to claim 1, wherein the ring element has a segmented design, wherein the first wall portion and/or the second wall portion likewise has a segmented design.

3. The fastening element according to claim 1, wherein the first wall portion and/or the second wall portion is held in a spread-open position, by the resilient connection, in an unloaded state.

4. The fastening element according to claim 1, wherein the first bearing area and/or the second bearing area permits a pivotable articulation of the first wall portion and/or the second wall portion.

5. The fastening element according to claim 4, wherein a pivotability in the first and second bearing areas is different.

6. The fastening element according to claim 1, wherein at least the second wall portion is formed of plastic.

7. The fastening element according to claim 6, wherein at least the second wall portion has harder and softer portions.

8. The fastening element according to claim 6, wherein at least the second wall portion is produced by means of a two-component injection molding technique.

9. The fastening element according to claim 6, wherein at least the second wall portion consists of plastic.

10. The fastening element according to claim 1, wherein at least one aperture is provided at least in the first bearing area.

11. The fastening element according to claim 1, wherein the first wall portion and the second wall portion are connected to each other resiliently.

\* \* \* \* \*